(12) United States Patent
Alexandersson et al.

(10) Patent No.: US 11,045,609 B2
(45) Date of Patent: Jun. 29, 2021

(54) PROTECTIVE ASSEMBLY FOR A SYRINGE

(71) Applicant: SHL Medical AG, Zug (CH)

(72) Inventors: Oscar Alexandersson, Haine (SE); Thomas Dietl, Falkenfels (DE)

(73) Assignee: SHL MEDICAL AG, Zug (CH)

( * ) Notice: Subject to any disclaimer, the term of this patent is extended or adjusted under 35 U.S.C. 154(b) by 183 days.

(21) Appl. No.: 16/150,395

(22) Filed: Oct. 3, 2018

(65) Prior Publication Data

US 2019/0105446 A1 Apr. 11, 2019

(30) Foreign Application Priority Data

Oct. 6, 2017 (EP) ..................................... 17195204

(51) Int. Cl.
*A61M 5/32* (2006.01)
*A61M 5/00* (2006.01)
*A61M 5/31* (2006.01)

(52) U.S. Cl.
CPC .......... *A61M 5/3202* (2013.01); *A61M 5/001* (2013.01); *A61M 5/321* (2013.01); *A61M 5/3204* (2013.01); *A61M 2005/3118* (2013.01); *A61M 2207/00* (2013.01)

(58) Field of Classification Search
CPC .............. A61M 5/3202; A61M 5/3204; A61M 5/3205; A61M 5/321; A61M 5/3213; A61M 5/3219; A61M 2005/3206; A61M 2005/3208; A61M 2005/3209; A61M 2005/3212; A61M 2005/3215; A61M 2005/3217; A61M 2005/3223; A61M 2005/3117; A61M 2005/3118; A61M 2005/312; A61M 5/001; A61M 2207/00; A61M 5/178; A61M 5/31; A61M 5/32
See application file for complete search history.

(56) References Cited

U.S. PATENT DOCUMENTS

2002/0062108 A1* 5/2002 Courteix ............. A61M 5/3202 604/198
2018/0333534 A1* 11/2018 Roervig ................ A61M 5/162

* cited by examiner

*Primary Examiner* — Jason E Flick
(74) *Attorney, Agent, or Firm* — McDonnell Boehnen Hulbert & Berghoff LLP

(57) ABSTRACT

The present invention relates to a needle shield assembly for a syringe (10), comprising an inner needle shield (16) which is flexible and designed to enclose a major part of a hollow injection needle (18) of said syringe; an outer needle shield (20) which is rigid and designed to enclose a major part of said inner needle shield (16), which outer needle shield (20) is arranged with a number of passages (22) for allowing sterilizing agents to reach said injection needle (18) during a sterilization process. The invention is characterised in that said needle shield assembly further comprises a cover element (24; 36; 46) arranged adjacent said passages (22) such as to prevent the interior of said injection needle (18) from being exposed to oxygen via said passages (22) of said outer needle shield (20) after said sterilization process.

19 Claims, 7 Drawing Sheets

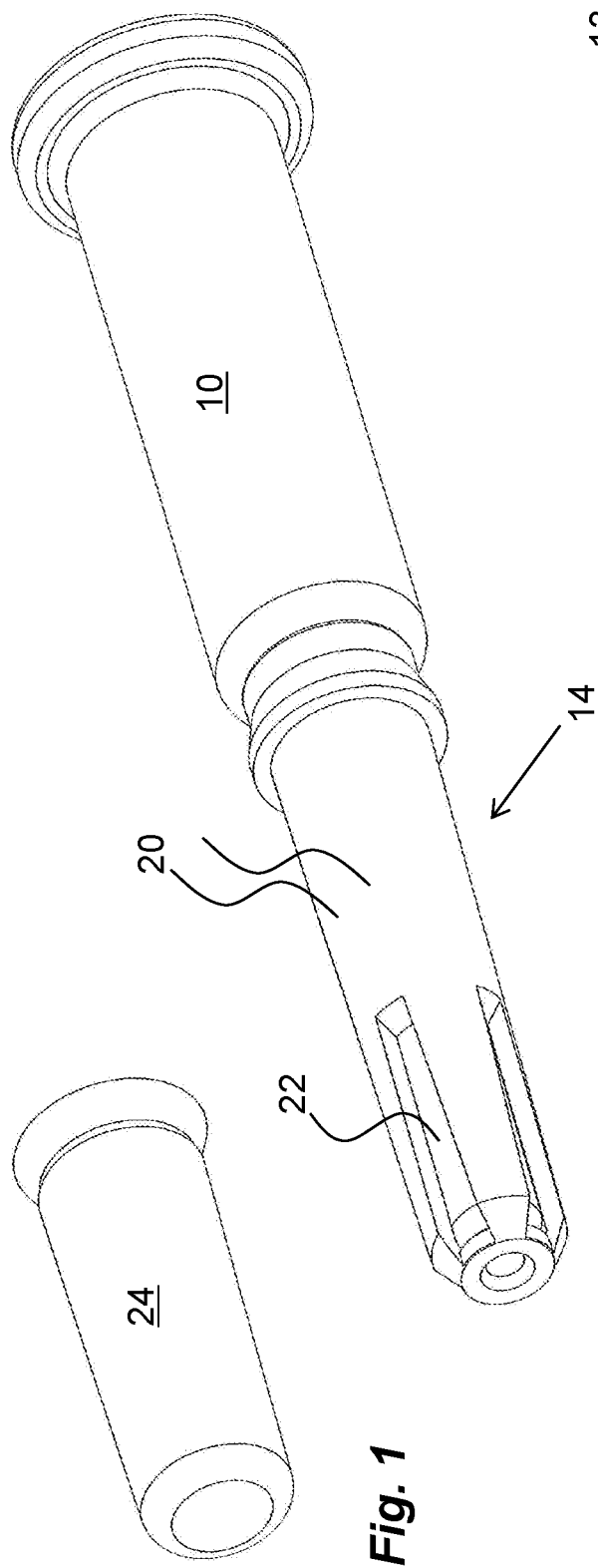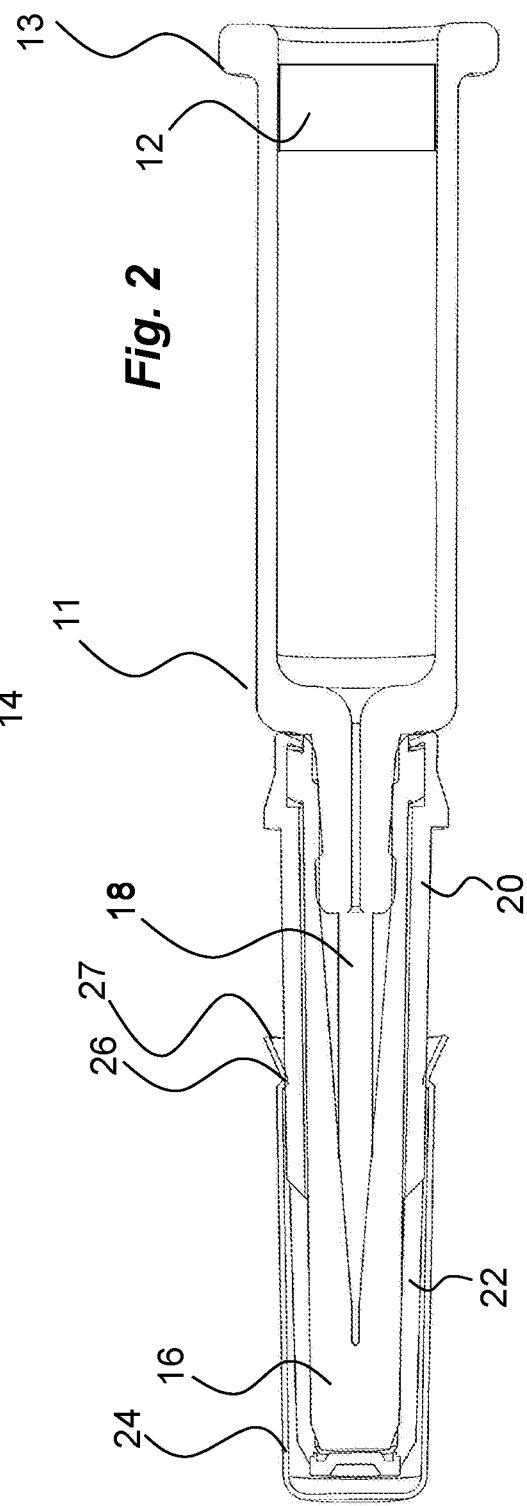

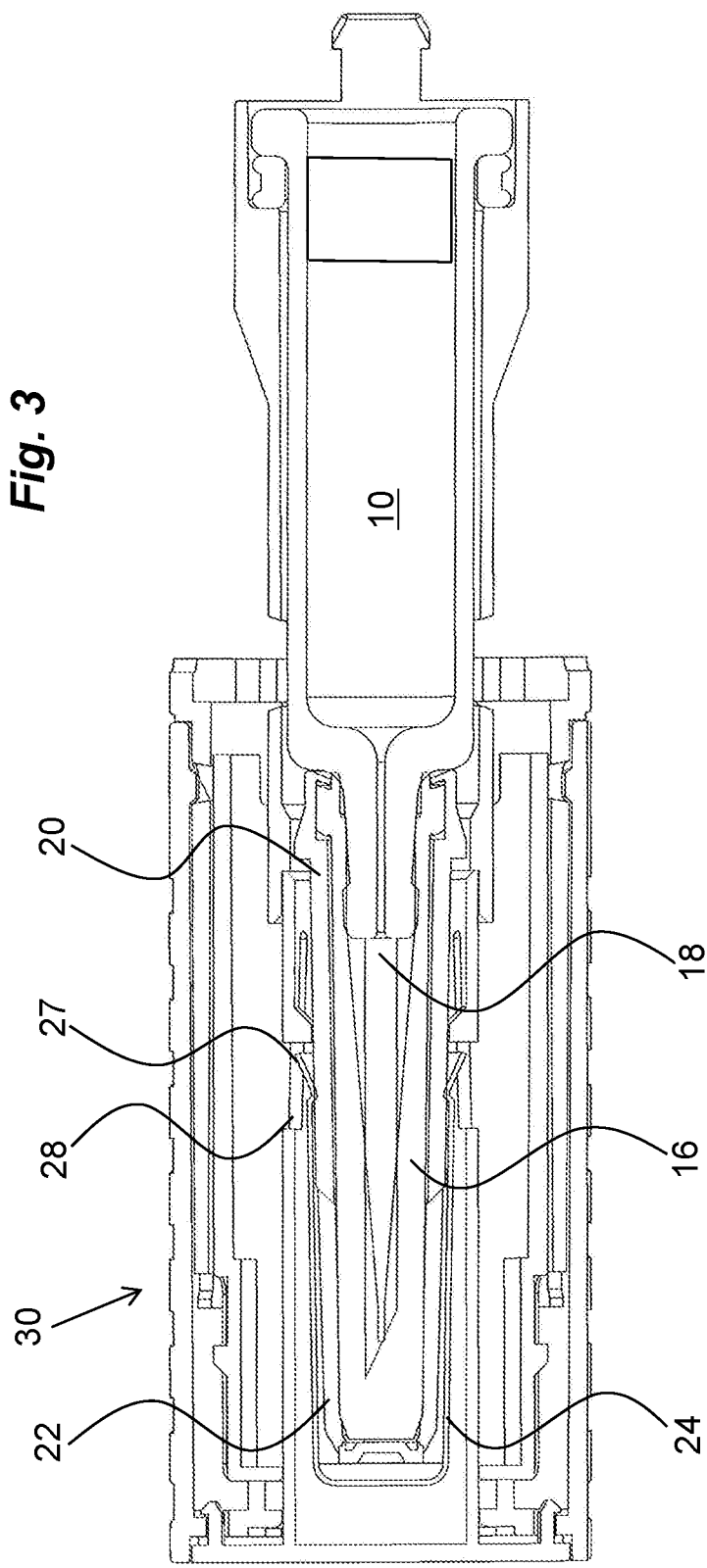

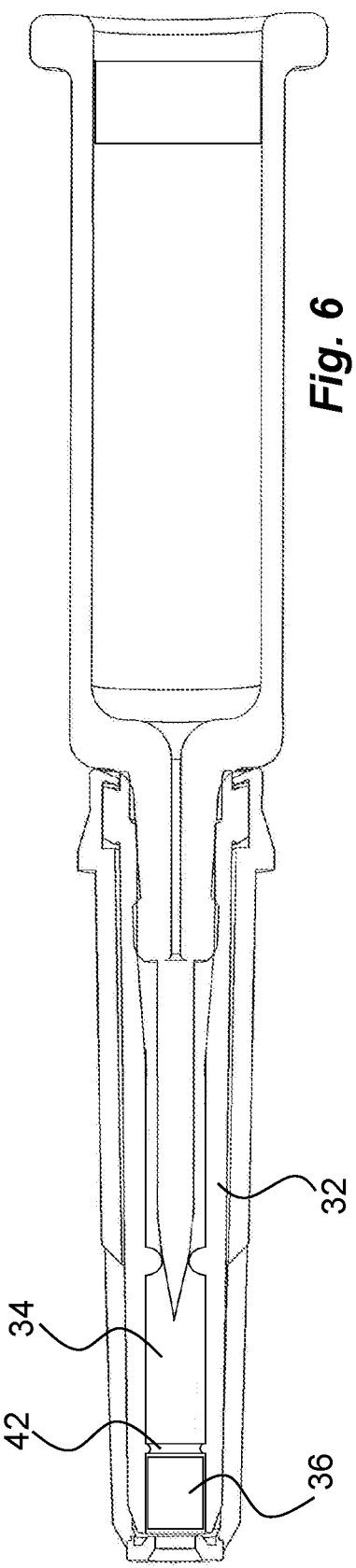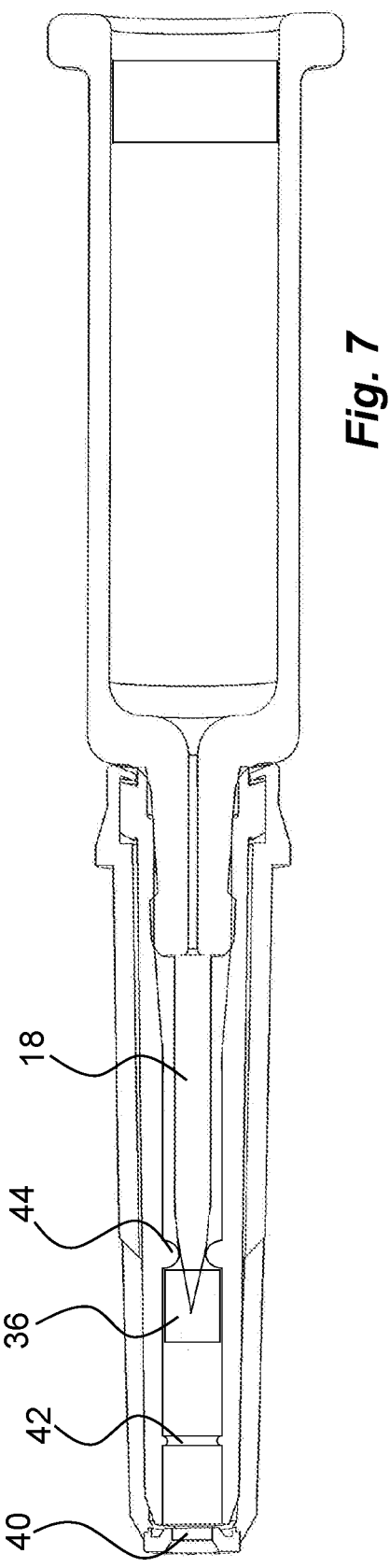

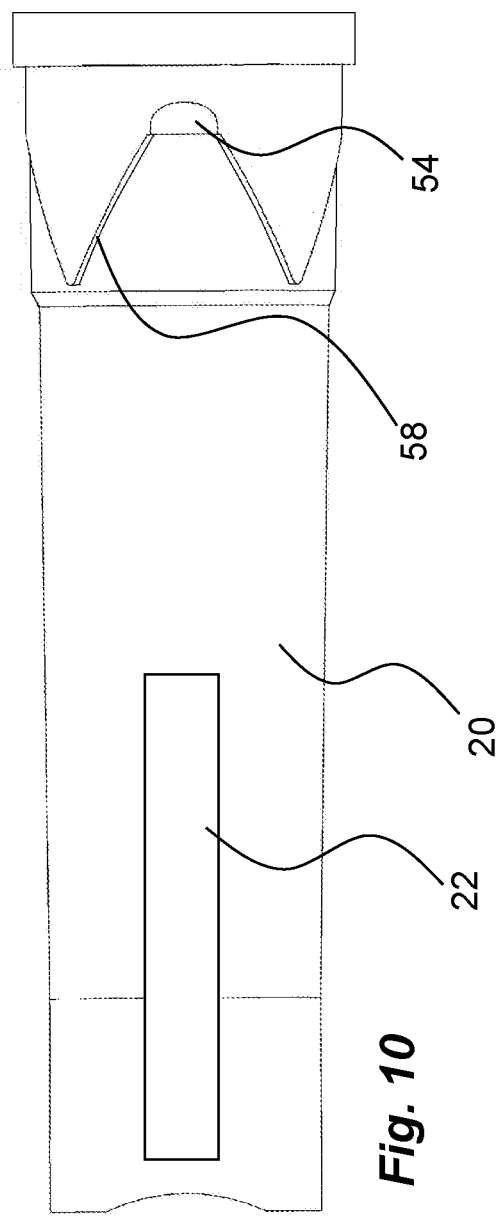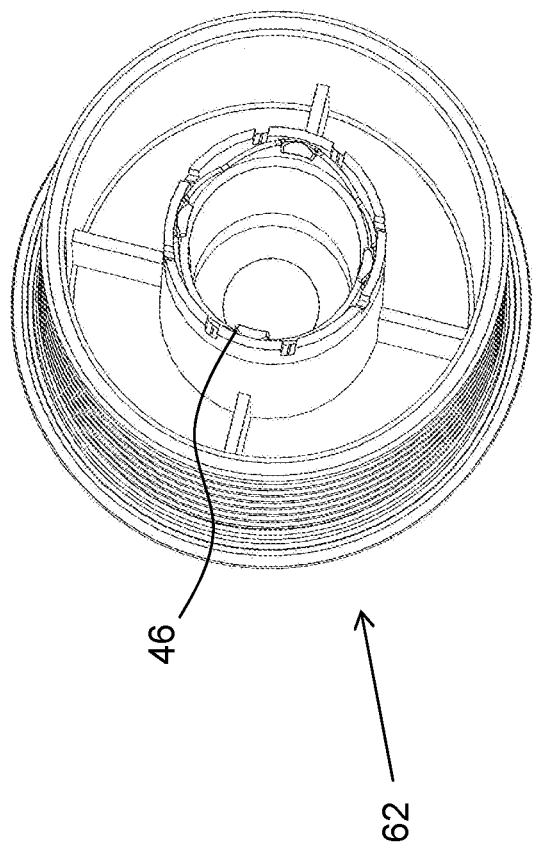

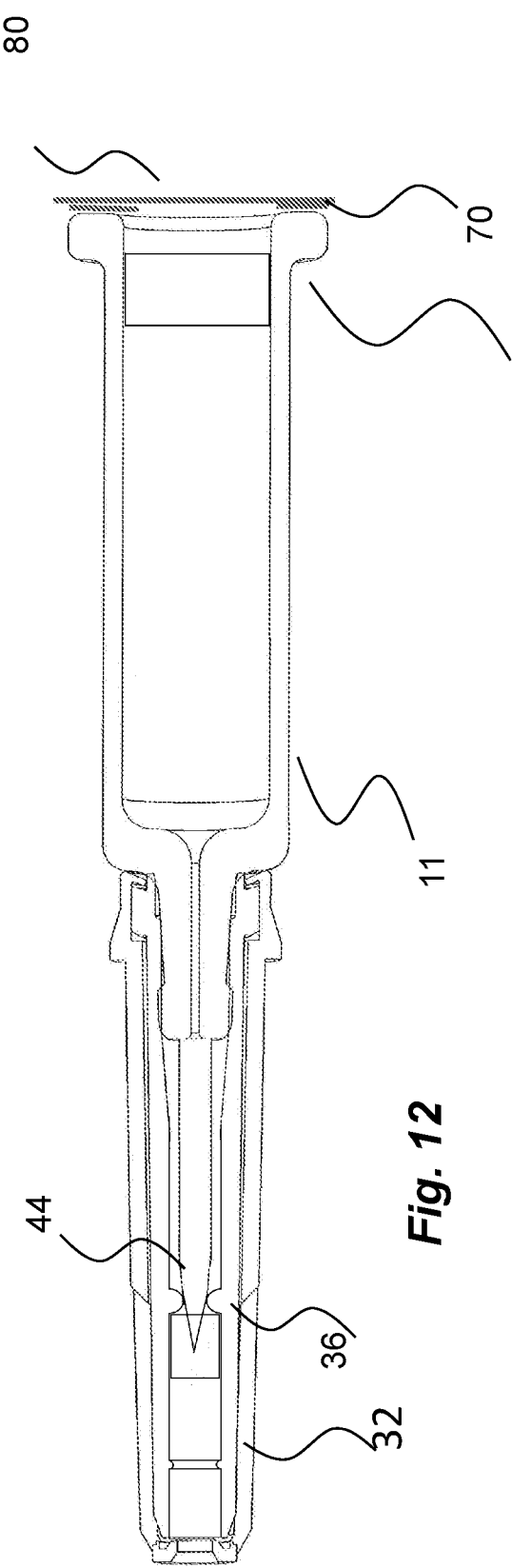
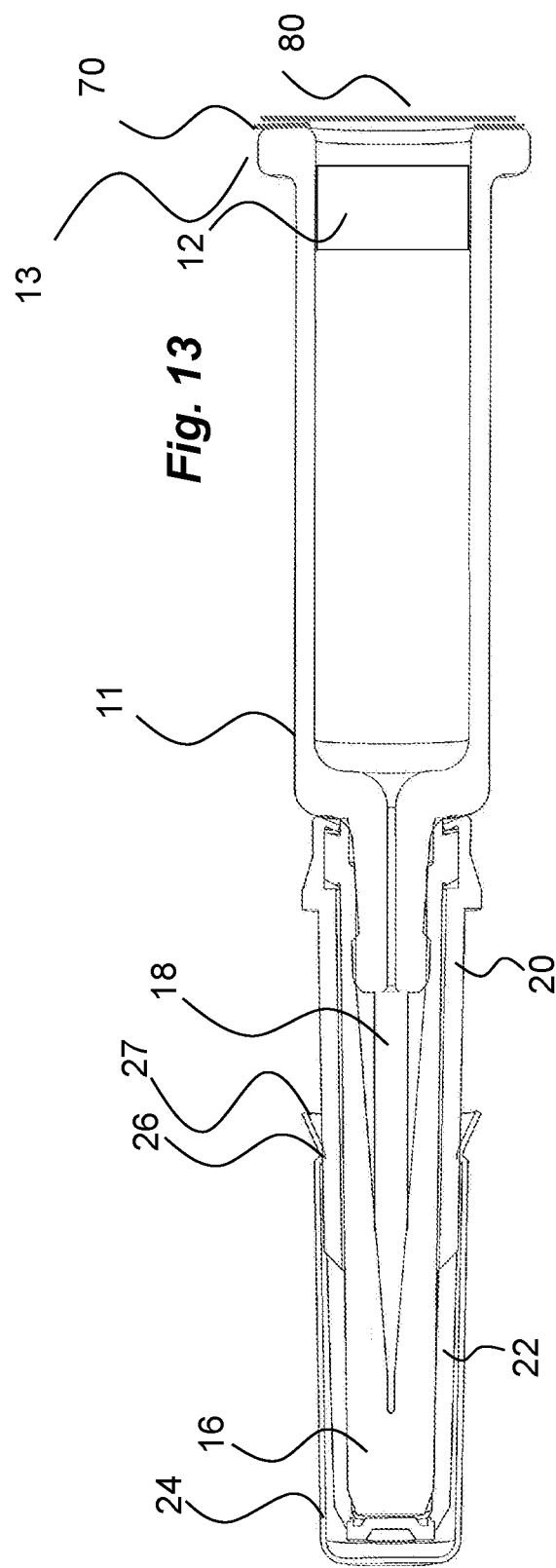

PROTECTIVE ASSEMBLY FOR A SYRINGE

CROSS REFERENCE TO RELATED APPLICATIONS

The present application claims priority to European Patent Application No. 17195204.7 filed Oct. 6, 2017, the entire disclosure contents of these applications are herewith incorporated by reference into the present application.

TECHNICAL AREA

The present invention relates to a protective assembly for a medicament container and in particular a syringe adapted for a medicament delivery device having a needle shield assembly comprising a rigid needle shield

BACKGROUND OF INVENTION

During the last decades, so called rigid needle shields or RNS have been used with medicament delivery devices. The RNS comprises a core of soft material such as rubber or thermoplastic elastomers with a shell or cover of harder material such as polypropylene. The combination provides increased safety when handling the needle shield during removal and re-attachment as well as increased protection of the needle if the attached needle shield is exposed to lateral or oblique forces that could potentially bend the needle.

In order to be able to sterilize the injection needle with an attached RNS, the RNS is provided with passages since the material of the outer cover is impermeable to sterilization gases such as ethylene oxide or steam. However, the inner core is gas permeable so that the sterilizing gas may reach the injection needle during the sterilization operation. A drawback with this solution is that the inner core or the inner flexible shield is permeable for air containing oxygen also and as the syringe may store a medicament for a time, the medicament might be oxidised and thus destroyed. Therefore, these is a need for a protective arrangement that at one hand allows sterilisation and on the other hand prevents the oxygen penetration into the syringe through the needle or the distal end.

BRIEF DESCRIPTION OF INVENTION

The aim of the present application is to provide a protective assembly for a syringe used in a medicament delivery device and allowing a sterilisation process for the syringe injection needle situated at a proximal end of the device and still able to prevent the oxidising of the medicament after the sterilisation within the syringe during the storage via the injection needle characterised by the features of the independent patent claim. The efficiency of the protective assembly can be increased further by a seal for preventing air and/or oxygen penetration also via a stopper at a distal end of the syringe for the medicament delivery device. Preferable embodiments form the subject of the dependent patent claims.

According to a main aspect, the protective assembly comprises a needle shield assembly that may comprise an inner needle shield which is flexible and designed to enclose a major part of a hollow injection needle of said syringe and an outer needle shield which is rigid and designed to enclose a major part of said inner flexible needle shield, which outer needle shield is arranged with a number of passages for allowing sterilizing agents to reach said injection needle during a sterilization process. This needle shield assembly may generally be regarded as a rigid needle shield or RNS.

According to a preferable embodiment, the protective assembly may further comprise a seal for sealing the distal end of the syringe.

The needle shield assembly may further comprise a cover element arranged adjacent the passages such as to prevent the interior of the injection needle from being exposed to oxygen via the passages of the rigid needle shield after a sterilization process. With such a cover element, it is ensured that oxygen from the environment cannot enter the injection needle and adversely affect the medicament contained in the syringe, which will prolong the shelf or storage life of the medicament. In this regard, the cover element may be made of an oxygen-impermeable material.

In one feasible embodiment, the cover element may comprise a sleeve arranged to be attached to and cover at least a part of the outer needle shield comprising the passages. The sleeve may in this regard be pushed onto the outer needle shield from a proximal end of the needle shield assembly. Further, the sleeve may comprise gripping elements capable of engaging an outer surface of the outer needle shield. This is a favourable solution in that it provides a removal of the needle shield assembly by a pulling action on the sleeve. In this regard, the gripping elements may comprise mainly friction enhancing elements, enhancing the friction between the sleeve and the outer needle shield. As an alternative, the gripping elements may comprise positive connecting elements.

As an alternative, the cover element may comprise a needle tip cover arranged to be movable inside the inner needle shield from a first position proximal of the injection needle to a second position enclosing at least a proximal part of the injection needle comprising the outlet of the passage of the injection needle.

The needle tip cover may be of a material allowing the injection needle to be imbedded therein. In addition, the flexible needle shield may further comprise an annular inwardly directed support element, and wherein the needle tip cover is moved into contact with the support element when moved to the second position.

Further with this alternative, the outer needle shield may be arranged with a proximally directed passage, through which passage the needle tip cover is accessible for movement from the first position to the second position. The needle tip cover may thus be moved between the positions by an appropriate tool fitting into the passage of the outer needle shield.

The needle shield assembly may further comprise connecting elements, designed for connection with a cap of a medicament delivery device. In this regard, the connecting elements may comprise mainly friction enhancing elements, enhancing the friction between the cap and the sleeve. As an alternative, the connecting elements may comprise positive connecting elements.

According to a further aspect, the cover element may be an integral part of a cap of a medicament delivery device. With this solution, the number of components of the medicament delivery device may be reduced with maintained functionality.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which FIG. 1 is a perspective view of a rigid needle shield mounted on a syringe and a first alternative of a cover according to the application, FIG. 2 is a cross-sectional view of the needle shield assembly of FIG. 1, FIG. 3 is a cross-sectional view of the needle shield assembly connected with a protective cap of a medicament delivery device, FIGS. 6 and 7 are cross-sectional views of a modification of the alternative of FIGS. 4 and 5, FIG. 10 is a modified outer shield for a needle shield assembly, and FIG. 11 is a perspective view of the third alternative integrated with a protective cap of a medicament delivery device.

FIG. 12 is further improved embodiment of FIG. 7 provided with a seal on the distal part of the syringe.

FIG. 13 is further improved embodiment of FIG. 2 provided with a seal on the distal part of the syringe.

DETAILED DESCRIPTION OF THE INVENTION

Figure 4:
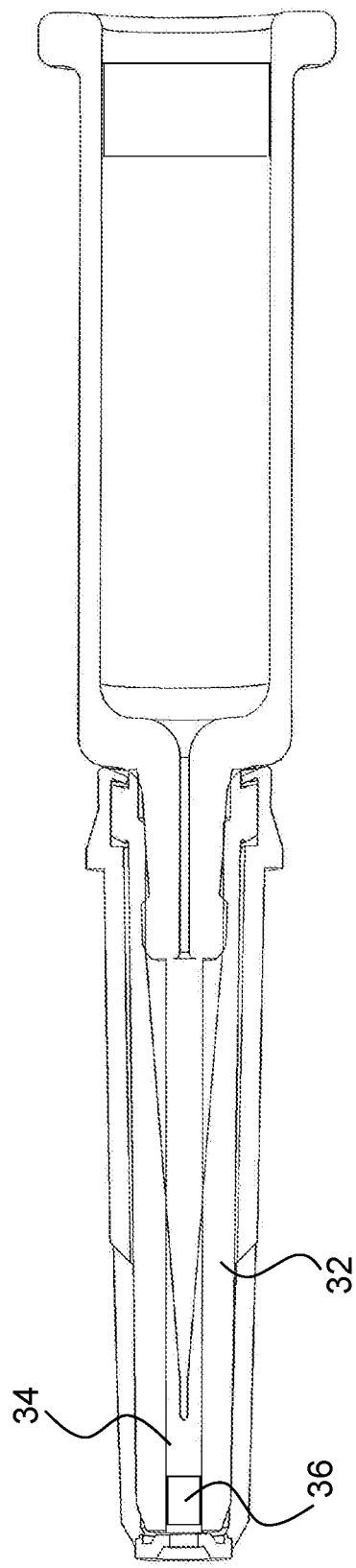
FIGS. 4 and 5 are cross-sectional view of a second alternative of a cover according to the application.

FIG. 1 shows a syringe 10 having a stopper 12 and being provided with a conventional rigid needle shield or RNS 14. The RNS 14 has an inner shield 16 of softer flexible material capable of surrounding and protecting an injection needle 18 of the syringe 10. The material of the inner shield 16 may be rubber, thermoplastic elastomers or other having the same type of material properties. The material of the inner shield 16 is permeable by gases such as sterilizing gases that are used to sterilize in particular the interior passage of the injection needle 18. The sterilizing gases may for example comprise ethylene oxide or steam. Outside the inner shield 16, an outer rigid shield 20 is placed coaxially. The outer shield 20 comprises a material that is much harder than the inner shield such as polypropylene, which also is impermeable to sterilizing gases. In order to allow sterilization, with the outer and inner shields mounted onto an injection needle, the outer shield 20 is arranged with passages 22, such as slits as shown in FIG. 1.

According to the present application, the aim is to prolong the shelf life of the syringe and to minimize the penetration of surrounding oxygen into in particular the passage of the injection needle, thereby preventing exposure of the medicament to oxygen, which would degrade the medicament. This may be done according to one solution shown in FIGS. 1 and 2, wherein the passages 22 in the outer shield are covered by a suitable closure. In the embodiment shown in FIGS. 1 and 2, the closure is in the form of an elongated tube 24 closed in a proximal end thereof and having an inner surface 24a. The tube 24 may have a diameter that corresponds to the outer diameter of the outer shield 20 such that a press fit is obtained when the tube 24 is pressed onto an outer surface 20a of the outer shield 20.

As an alternative or in addition, the distal end of the tube 24 may be provided with an annular inwardly directed ledge 26 that will provide a firm contact with the outer surface of the outer shield 20. Further, in order to provide a support for pulling the whole unit with the RNS and the closure off the injection needle 18 when the syringe 10 is to be used for delivering a dose, the distal end of the tube 24 may be arranged with an outwardly directed portion 27, in the embodiment shown outwardly inclined. This portion may then fit into a recess 28 in a protective cap 30 that is removed when a dose is to be administered, as seen in FIG. 3.

Figure 5:
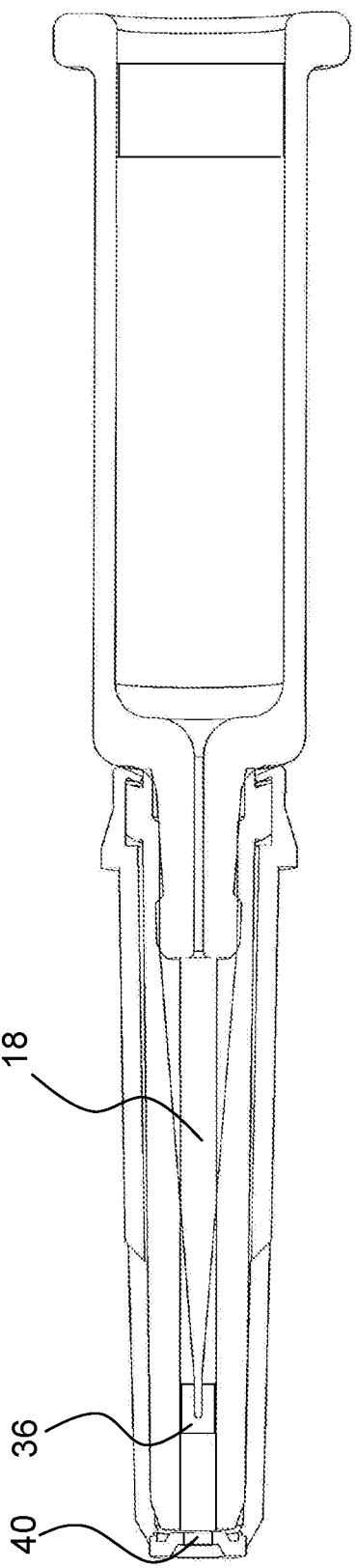

FIGS. 4 and 5 show a variant of protecting the inner passage and thus the medicament from oxygen after sterilization. In this case an inner shield 32 is arranged with a generally tubular passage 34 in its proximal end in which the tip of the injection needle 18 fits when the RNS is put onto the injection needle 18. Inside the tubular passage a needle tip cover 36 is arranged movable, which needle tip cover 36 is made of a material impermeable to oxygen. Further the proximal end surface of an outer shield 38 is arranged with a central passage 40, whereby the tubular passage 34 of the inner shield 32 is accessible. When an injection needle is to be sterilized, the needle tip cover 36 is in a proximal position as seen in FIG. 4 whereby the injection needle 18 can be completely exposed to sterilization gases. After sterilization, a suitable tool is inserted through the central passage 40 of the outer shield 38 and the needle tip cover 36 is pushed onto the tip of the injection needle 18, whereby the passage in the injection needle is closed. In this regard, the needle tip cover 34 may be of a flexible material allowing penetration by the injection needle. Alternatively or in addition, the needle tip cover 34 may have a closed recess or passage having a diameter somewhat smaller than the outer diameter of the injection needle 18, into which recess the tip may fit.

A variant to the embodiment of FIGS. 4 and 5 is shown in FIGS. 6 and 7. Here the inner passage 34 is arranged with a first inwardly directed rather small ledge 42 that will prevent the needle tip cover 36 from moving in the passage 34 until the needle tip cover 36 is pushed passed the first ledge 42 by an appropriate tool. By this it is prevented that the needle tip cover 36 is unintentionally blocking the tip of the injection needle 18 during the sterilization sequence. When the sterilization sequence has been performed the needle tip cover 36 is pushed past the first ledge 42 and onto the tip of the injection needle 18, FIG. 7. With this variant a second ledge 44 may be arranged that preferably is larger than the first ledge 42, where the second ledge 44 functions as a stop surface for the needle tip cover 36, ascertaining that the needle tip cover 36 cannot be pushed too far onto the needle tip.

Figure 8:
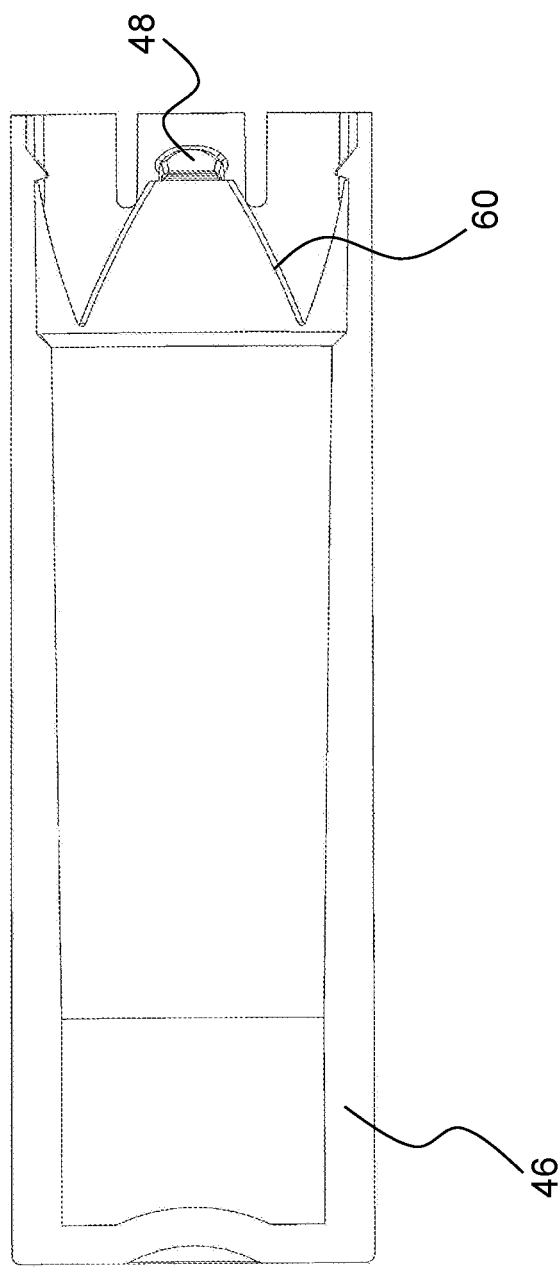
FIG. 8 is a cross-sectional view of a third alternative of a cover according to the application.
Figure 9:
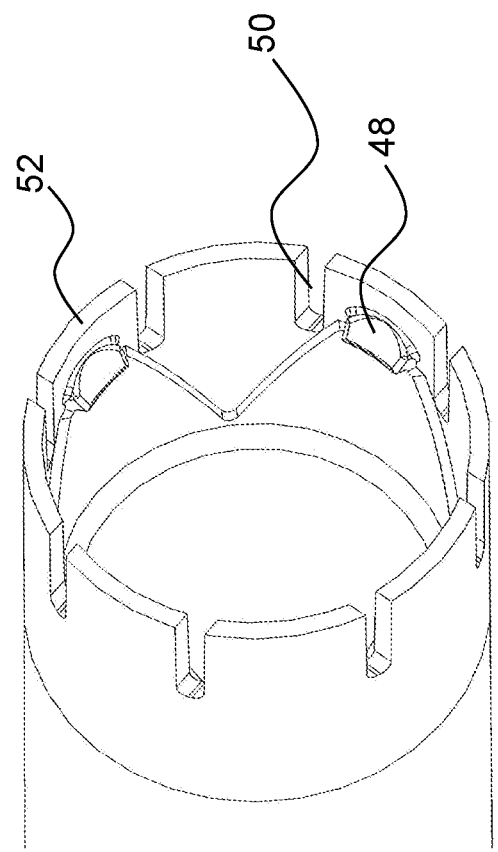
FIG. 9 is a perspective view of an end area of the third alternative of FIG. 8.

A further alternative is shown in FIGS. 8 to 11. Here a closure is designed as a cap 46, FIGS. 8 and 9 that encloses a major part of the outer surface of the outer shield 20 of the RNS. The cap 46 may be pushed onto the outer shield 20 of the RNS after sterilization. Preferably the RNS is supported in the distal end when the cap 46 is pushed onto the RNS. The cap 46 may further preferably be arranged with gripping elements 48 that are capable of providing a grip on the surface of the outer shield 20 in order to be able to remove the RNS when the syringe is to be used. In one example the gripping elements may comprise wedge-shaped inwardly directed ledges 48 as seen in FIGS. 7 and 8. Alternatively the wedge-shaped ledges 48 and the length of the cap may be designed such that the ledges 48 are placed behind the distal end surface of the outer shield 20 when the cap is mounted onto the RNS. In order to facilitate the assembly of the outer cap with the cap, a number of longitudinal slits 50 may be provided around the distal end area of the cap 46, forming a number of distally directed tongues 52 that tare flexible in the generally radial direction, wherein the ledges 48 are positioned on the inner surfaces of the tongues 52. With this solution, the ledges 48 may flex out radially during the mounting of the cap 46 onto the RNS, wherein the tongues 52 may flex back inwards after the ledges 48 have passed the distal end of the outer shield 20 of the RNS. As an alternative, the outer shield 20 may be specially designed to accommodate ledges of the outer cap, FIG. 10, for example having recesses 54 or ledges that cooperate with the ledges 48 of the cap 46. Further, in order to obtain a rotational lock between the outer shield 20 and the cap, support surfaces may be arranged. In the embodiment shown, the outer surface of the outer cap 20 is arranged with proximally directed surfaces 58 that are inclined in relation to the longitudinal axis of the outer shield. These surfaces 58 are designed and arranged to cooperate with distally directed surfaces 60 that also are inclined such that when the outer shield is connected to the cap, the inclined surfaces 58, 60 are moved in abutment with each other.

According to a development of the last embodiment, the cap 46 may be an integral part of a safety cap 62 as seen in FIG. 11. With this solution, fewer components are needed for obtaining the same function.

According to a further improvement, for preventing air and/or oxygen from entering the syringe 10 interior containing the medicament, according to the embodiment as illustrated in FIGS. 2-5 and the other embodiment as illustrated in FIGS. 6-7, a hermetic seal 80 or a suitable protector in a suitable form can be also arranged at the distal end 13 of the syringe 10 for a storage time as illustrated in FIGS. 12 and 13. The seal 80 might be e.g. attached by a clue layer 70 to the distal end 13 of the syringe 10. When the syringe 10 is to be used for performing an injection, a plunger rod (not shown) of the medicament delivery device, in which the prefilled syringe 10 is to be inserted, is able to penetrate this seal 80 and to force a stopper 13 forward performing the injection. The medicament delivery device can be any type of the known devices, e.g. a pen injectors or the like, the device having a plunger rode which might be activated either manually or by a driving unit of the device. The driving unit might have either a mechanical or electrical drive.

It is to be understood that the embodiments described above and shown in the drawings are to be regarded only as non-limiting examples and that the protective assembly may be modified in many ways within the scope of the patent claims.

The invention claimed is:

1. An assembly for a syringe, the syringe having a distal end and a proximal end, where the assembly comprises:
   an inner needle shield which is flexible and designed to enclose a major part of a hollow injection needle operably engaged with the syringe;
   an outer needle shield which is rigid and designed to enclose a major part of the inner needle shield and having an outer surface, where the outer needle shield is arranged with a number of passages that allow sterilizing agents to reach the injection needle during a sterilization process; and
   a cover element having an inner surface that forms a press fit with the outer surface of the outer needle shield adjacent the passages such that the passages are covered to prevent the interior of said injection needle from being exposed to oxygen via said passages of said outer needle shield after said sterilization process,
   wherein a distal end of the inner surface of the cover element comprises a gripping element that forms a grip on the outer surface of the outer needle shield such that outer needle shield and the inner shield will be removed from the syringe when the cover element is moved axially.

2. The protective assembly according to claim 1, further comprises a seal for the distal end of the container.

3. The assembly of claim 2, wherein said cover element comprises a needle tip cover arranged to be movable inside said inner needle shield from a first position proximal of said injection needle to a second position enclosing at least a proximal part of said injection needle.

4. The assembly of claim 1, wherein the cover element is made of an oxygen-impermeable material.

5. The assembly of claim 1, wherein the cover element comprises a sleeve arranged to be attached to and cover at least a part of the outer needle shield that comprises the passages.

6. The assembly of claim 5, wherein said sleeve comprises gripping elements configured to engage an outer surface of the rigid needle shield.

7. The assembly of claim 6, wherein the gripping elements comprise friction enhancing elements that enhance friction between said sleeve and said outer needle shield.

8. The assembly of claim 5, wherein said needle tip cover is of a material allowing said injection needle to be imbedded therein.

9. The assembly of claim 5, wherein said inner needle shield further comprises an annular inwardly directed support element, and wherein said needle tip cover is moved into contact with said support element when moved to the second position.

10. The assembly of claim 5, wherein said outer needle shield is arranged with a proximally directed passage, through which passage said needle tip cover is accessible for movement from said first position to said second position.

11. The assembly of claim 10, wherein the connecting elements comprise mainly friction enhancing elements, enhancing the friction between said cap and said sleeve.

12. The assembly of claim 10, wherein the connecting elements comprise positive connecting elements.

13. The assembly according to claim 1, wherein said cover element is an integral part of a cap of a medicament delivery device.

14. The assembly of claim of claim 1, wherein the inner surface of the cover element further comprises a gripping element configured as an inwardly protruding ledge that is operatively engaged with a distal end surface of the outer needle shield.

15. The assembly of claim of claim 14, wherein the gripping element is wedged-shaped and forms a grip with the outer needle shield.

16. The assembly of claim of claim 1, wherein a distal end of the cover element further comprises a plurality of slits.

17. The assembly of claim of claim 16, wherein the plurality of slits form distally directed tongues that flex radially outward when engaging the outer surface of the outer needle shield.

18. The assembly of claim of claim 1, wherein the inner surface of the cover element further comprises a plurality of wedged-shaped gripping elements that are positioned behind a distal end of the outer needle shield and are operatively engaged such that outer needle shield and the inner shield will be removed from the syringe when the cover element is moved proximally relative to the syringe.

19. A medicament delivery device comprising a protective assembly according to claim 1.

* * * * *